United States Patent
Dumaresq-Lucas et al.

(10) Patent No.: US 6,796,965 B2
(45) Date of Patent: Sep. 28, 2004

(54) SYRINGE WITH FILTER, AND FILTER THEREFOR

(76) Inventors: Alison Jayne Dumaresq-Lucas, Twin Oaks, Todmore, Greatham, Hampshire (GB), GU23 6AR; Gerald D. Day, 72 Gospel Farm Road, Acocks Green, Birmingham (GB), B27 7LJ (*) Notice: Subject to any disclaimer, the term of this patent is extended or adjusted under 35 U.S.C. 154(b) by 255 days.

(21) Appl. No.: 09/789,043

(22) Filed: Feb. 20, 2001

(65) Prior Publication Data

US 2001/0007062 A1 Jul. 5, 2001

Related U.S. Application Data

(62) Division of application No. 09/480,542, filed on Jan. 10, 2000, now abandoned.

(30) Foreign Application Priority Data

Jan. 12, 1999 (GB) .............................................. 9900459

(51) Int. Cl.[7] .............................................. A61M 5/00
(52) U.S. Cl. ........................................ 604/190; 604/247
(58) Field of Search .............................. 604/27, 30–33, 604/181, 187, 190, 218, 236, 246–247, 249, 251–252, 255–256, 165.01, 167.01–167.04, 200; 137/493.9, 550

(56) References Cited

U.S. PATENT DOCUMENTS

| | | | |
|---|---|---|---|
| 3,757,780 A | | 9/1973 | Ishikawa |
| 3,938,513 A | * | 2/1976 | Hargest ...................... 604/190 |
| 4,066,079 A | | 1/1978 | Chiarolla |
| 4,332,249 A | * | 6/1982 | Joslin ......................... 604/36 |
| 4,391,274 A | | 7/1983 | Kagan |
| 4,488,961 A | | 12/1984 | Spencer |
| 5,494,044 A | | 2/1996 | Sundberg |
| 5,618,266 A | * | 4/1997 | Liprie ......................... 604/21 |

FOREIGN PATENT DOCUMENTS

WO    WO 90/13261    11/1990

* cited by examiner

Primary Examiner—Loan H. Thanh
(74) Attorney, Agent, or Firm—Browning Bushman P.C.

(57) ABSTRACT

A syringe comprising a one-way filter which permits flow of fluid into the syringe unfiltered but which filters the fluid when expelled from the syringe.

4 Claims, 6 Drawing Sheets

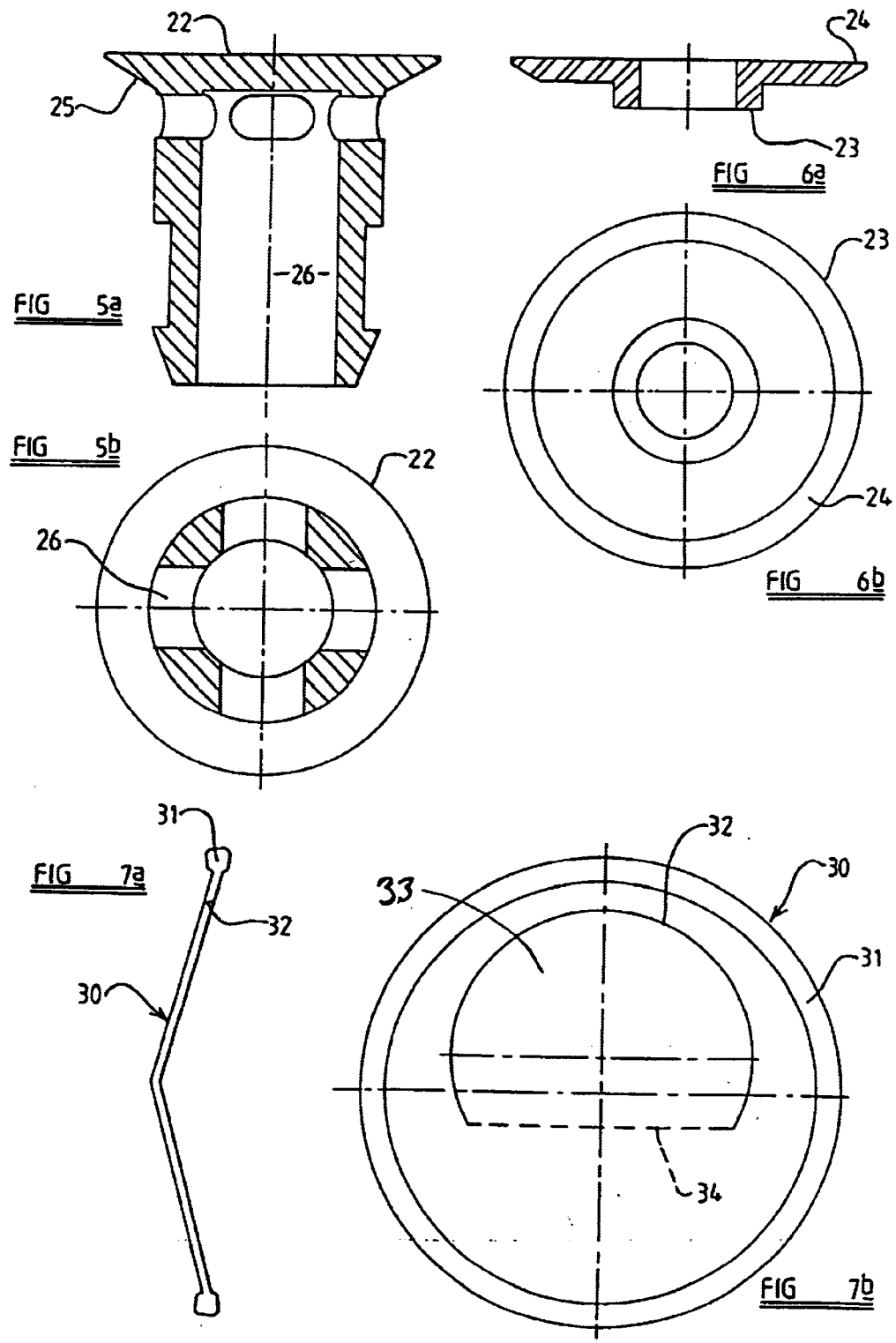

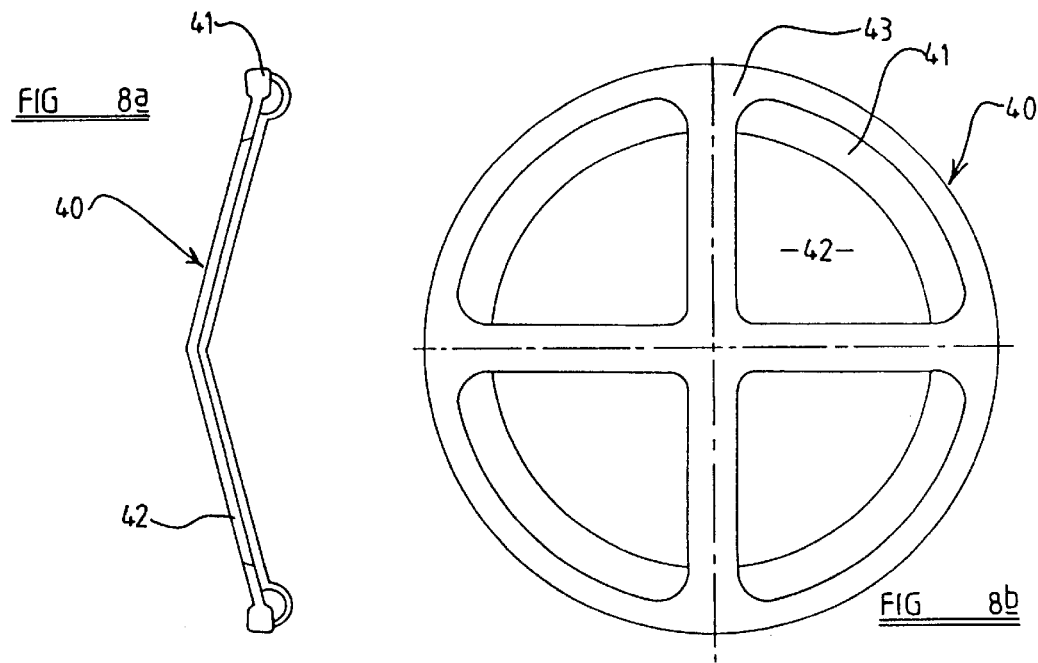
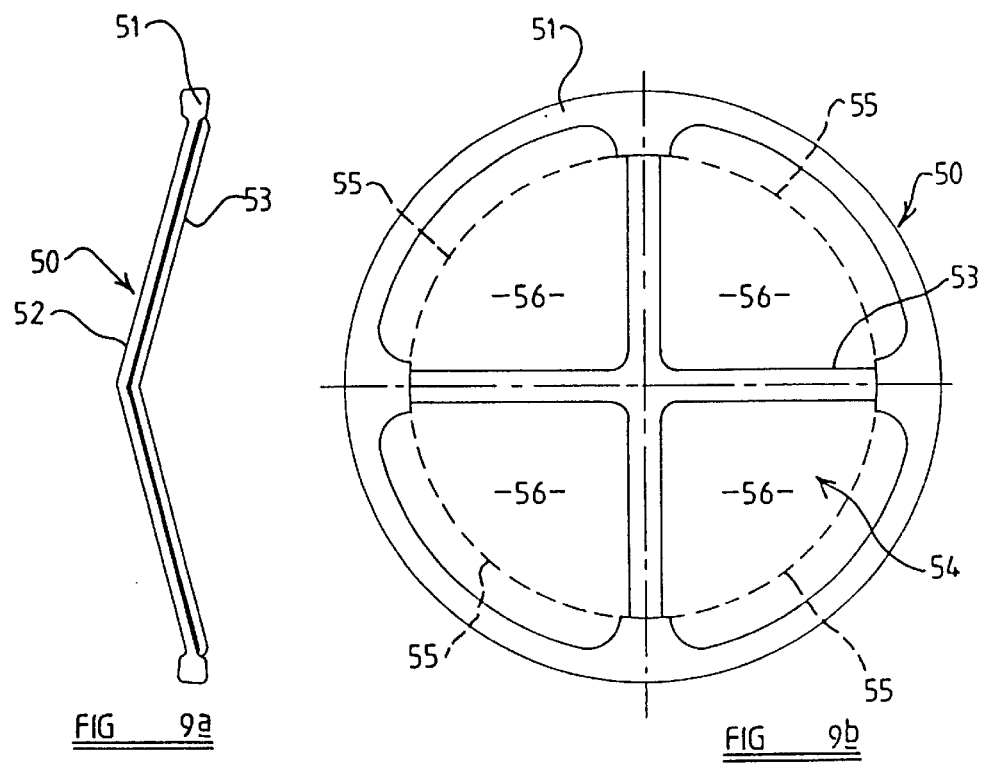

SYRINGE WITH FILTER, AND FILTER THEREFOR

This application is a divisional of U.S. patent application Ser. No. 09/480,542, filed on Jan. 10, 2000, now abandoned.

BACKGROUND TO THE INVENTION

The invention relates to syringes, and in particular, although not exclusively, to such syringes for medical use, incorporating filters, and to filters for incorporation in such syringes.

When fluids are given to patients from a bag, this generally being known as by means of a drip, an in-line filter is used to ensure that no small particulates left from the manufacturing process enter then body. The filters are generally incorporated in the line used to deliver the fluid during it's manufacture, and sterilised as part of the manufacture process.

Patients are also given fluids as injections using a syringe to draw up the appropriate volume of fluid from a supply container and then inject it into the patient. No filtration is used and therefore small particulate by products from the production process may for the syringe, or needle, may be injected into the patient. Clearly this is undesirable, and a suitable form of filtration should be provided.

It is an object of the present invention to provide a syringe which mitigates the above identified problem.

SUMMARY OF THE INVENTION

According to the present invention there is provided a syringe comprising a one-way filter which permits flow of fluid into the syringe unfiltered but which filters the fluid when expelled from the syringe.

Preferably the one-way filter comprises a filter membrane through which the fluid passes when expelled from the syringe.

The filter membrane may be fixed relative to the syringe and the one-way filter comprises valve means which open when the fluid is sucked into the syringe to permit the fluid to by-pass the filter membrane, and closes prior to fluid being expelled from the syringe such that the fluid must pass through the filter membrane.

The valve means may comprise a valve member providing first and second valve surfaces and a passage there through and being slidable in a fixed member which provides first and second valve seats, the first valve surface closing onto the first valve seat when fluid is drawn into the syringe to by-pass the filter membrane fluid entering the syringe through the passage, the second valve surface closing onto the second valve seat, to close the passage and ensure that the fluid must pass through the filter membrane, prior to the fluid being expelled from the syringe.

In an alternative form the valve means comprise at least one passage through or around the filter membrane and at least one valve member of resilient material which opens the passage when fluid is drawn into the syringe and closes the passage prior to fluid being expelled from the syringe.

The filter membrane may be flexible such that at least a portion of it is moved inwardly of the syringe when fluid is sucked into the syringe to open a passage and permit fluid to by-pass the filter membrane, the portion being moved back to close the passage prior to fluid being expelled from the syringe such that the fluid must pass through the filter membrane.

The filter membrane may have a cut there through to form a flap portion and a hinge line, the flap portion being the portion of the filter membrane which moves.

The filter membrane may be secured to a spring member which moves in response to the flow of fluid into or our of the syringe and causes the filter membrane to move with it. Conveniently the spring member comprises a cross formation of either side of the filter membrane, the filter membrane being retained between them.

BRIEF DESCRIPTION OF THE DRAWINGS

Examples of syringes according to the invention will now be described, by way of example only, with reference to the accompanying drawings in which:

FIGS. 5 & 6 illustrate in (a) cross section and (b) plan view first and second sub-members respectively of a valve member of the one-way filter assembly of the embodiment of FIGS. 1 and 2; and FIGS. 7 to 12 illustrate in (a) cross section and (b) plan view six alternative filters for embodiments of the invention;

DESCRIPTION OF THE PREFERRED EMBODIMENTS

Figure 1:
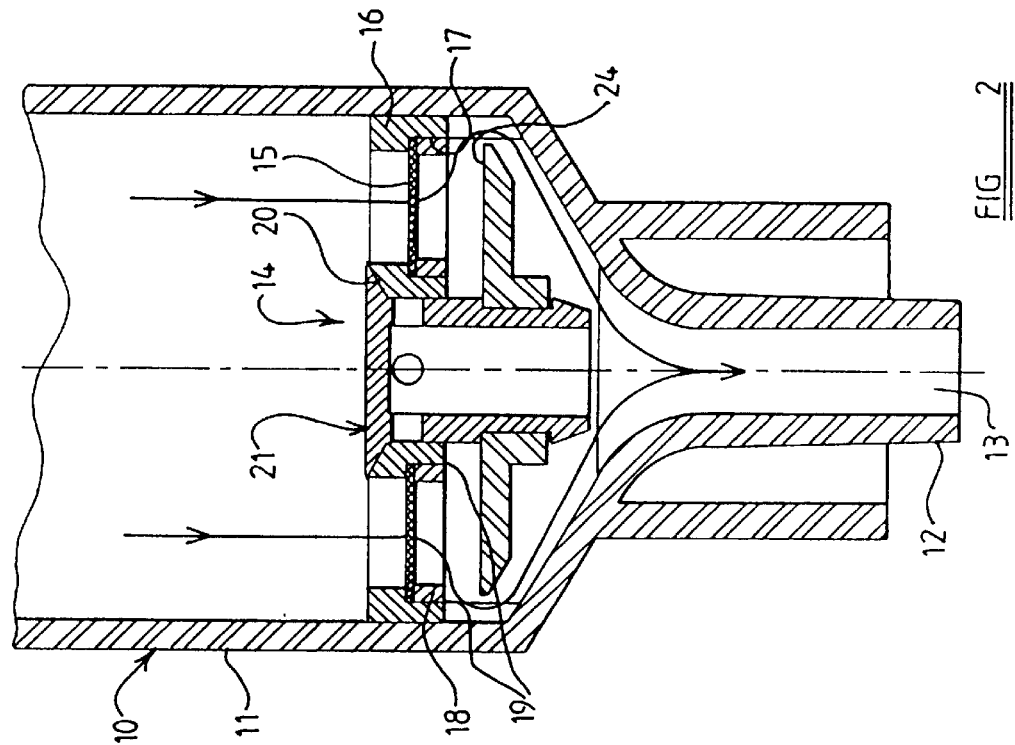
FIG. 1 is a cross section through a first embodiment of a syringe according to the invention, showing the flow of fluid into the syringe.
Figure 2:
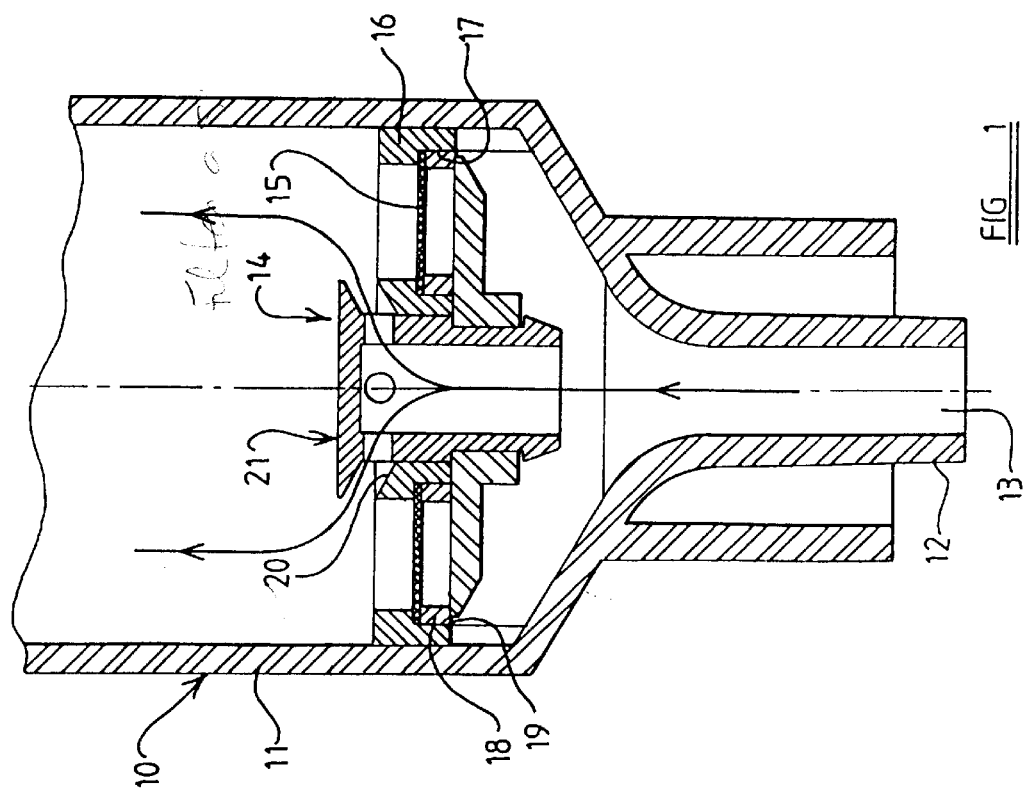
FIG. 2 is a cross section through the embodiment of FIG. 1, showing the flow of fluid out of the syringe.
Figures 3A, 3B, 3C:
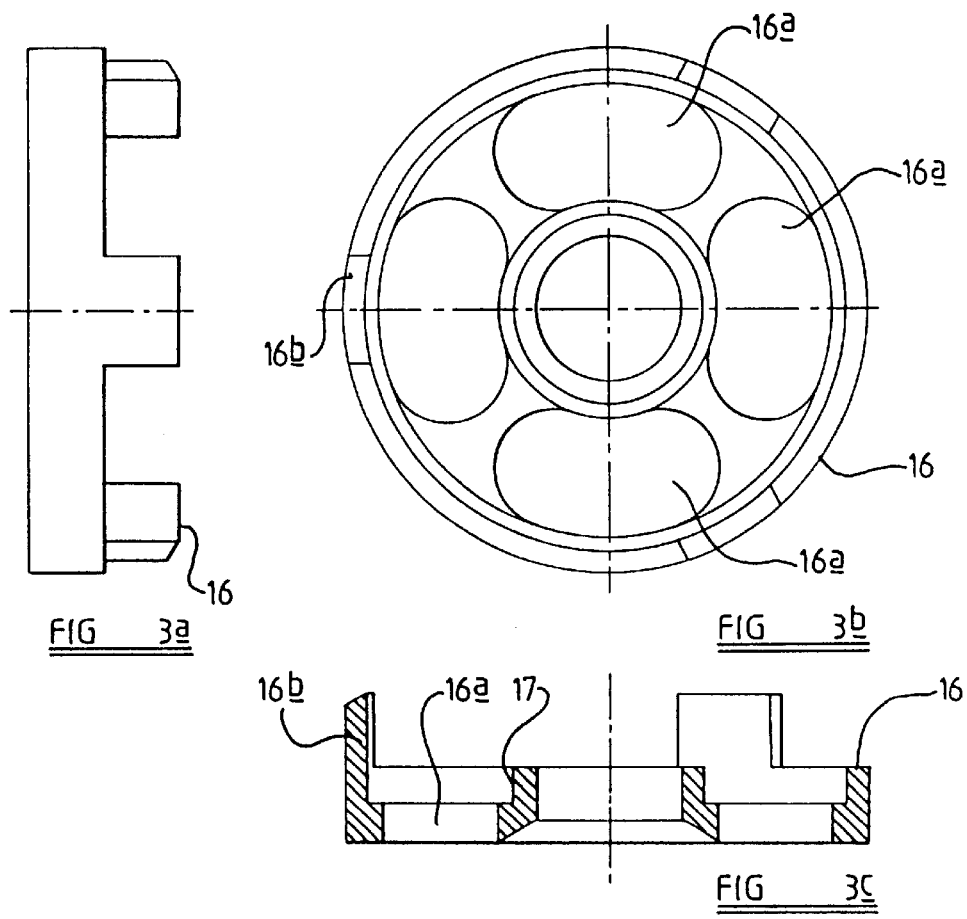
FIG. 3 illustrates in (a) side view, (b) plan view and (c) cross section, a first annular member of the one-way filter assembly of the embodiment of FIGS. 1 and 2.
Figures 4A, 4B:
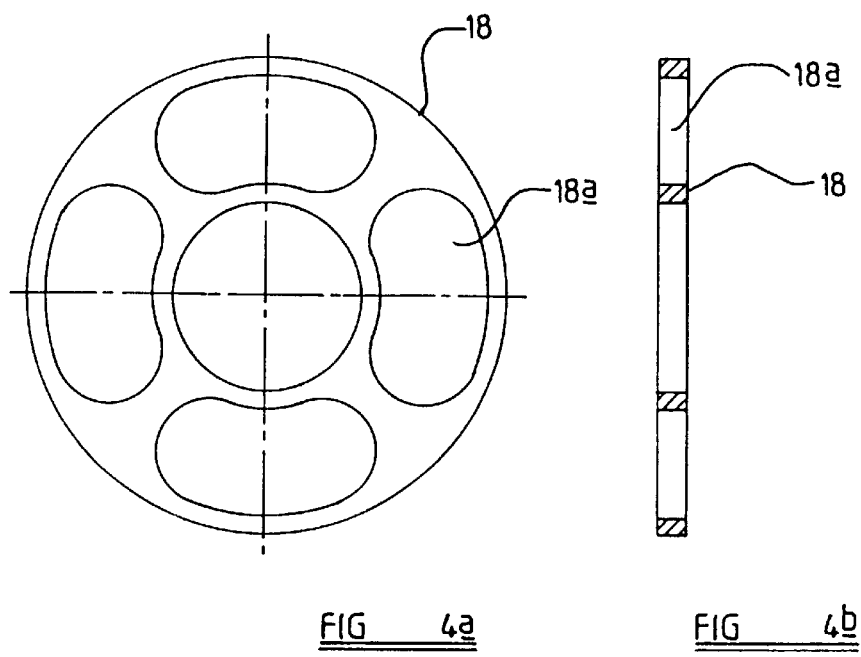
FIG. 4 illustrates in (a) plan view and (b) cross section a second annular member of the of the one-way filter assembly of the embodiment of FIGS. 1 and 2.

Referring first to FIGS. 1 to 6, a first embodiment of a syringe 10 according to the invention will be described. The syringe 10 comprises a main body 11 for receipt of fluid to be injected, a needle engagement formation 12 to which a needle (not shown) is attached in use, an opening 13 through which fluid may pass into or out of the syringe 10 and a plunger (not shown) for control of the flow of fluid into and out of the syringe 10. The syringe 10 also comprises a one-way filter assembly 14.

The one-way filter assembly 14 comprises an annular filter membrane 15 fixed relative to the main body 11 of the syringe 10 by means of a first annular member 16 which is a push fit within the main body 11. The first annular member 16 has a recess 17 into which the filter 15 is located and retained by a second annular member 18. Both annular members 16, 18 comprise a plurality of holes 16a, 18a there through, in this case four, which leave the majority of the area of the filter membrane 15 exposed. Preferably, as illustrated the two sets of holes 16a and 18a are of substantially the same size and shape, and when the assembly 14 is assembled they are arranged to overlay each other. This ensures that the maximum area of the filter membrane 15 is left exposed and that it is supported as well as possible.

The first annular member 16 also comprises three legs 16b spaced around it's periphery which space the member 16 from the needle attachment formation 12 of the syringe 10.

The first and second annular members 16, 18 combine to form a first valve seat 19 facing towards the needle attachment formation 12, whilst the first annular member 16 forms a second valve seat 20 facing the main body 11 of the syringe 10.

A valve member 21 comprises, for manufacturing convenience only, first and second sub-members 22, 23, the second sub-member 23 being a push fit onto first sub-member 22 to form the valve member 21. The valve member 21 is located in the centre of the first and second annular members 16, 18 such that it can move relative to those members 16, 18. The valve member 21 provides a first valve surface 24 which is adapted to abut and seal against the first valve seat 19, and a second valve surface 25 which is adapted to abut and seal against the second valve seat 20. The valve member 21 also comprises a passage 26 there through.

The valve member 21 operates as follows when the syringe 10 is in use. When the plunger is withdrawn to draw fluid into the syringe 10 the fluid pushes the valve member 21 upward such that the first valve surface 24 abuts and seals against the first valve seat 19, fluid then passes through the passage 26 in the valve member 21 into the main body 11 of the syringe 10, as shown by the arrows in FIG. 1. When the plunger is depressed to expel the fluid from the syringe 10 the fluid passes through the filter membrane 15 and pushes the valve member 21 such that it moves towards the opening 13. This movement opens the first valve surface 24 from the first valve seat 19 and closes the second valve surface 25 onto the second valve seat 20, the flow of fluid being illustrated by the arrow in FIG. 2. Thus fluid passing into the syringe 10 is not filtered whilst fluid passing out is filtered, the filter assembly 14 acting a s a one-way filter.

Referring now to FIG. 7 a first alternative filter embodiment will be described. The one-way filter 30 comprises a single piece of thermally moulded filter material of known kind. The filter 30 has an outer ring 31 adapted to be a snap fit into a recess formed within the main body of a syringe (not shown). The filter 30 is of a conical form as best seen in cross section, and is intended to be fitted into the syringe with the apex of the cone towards the opening and needle. A cut 32, being an arc of a circle, is provided in the central region of the filter 30. This cut 32 forms a flap portion 33 and a hinge line 34 (shown in chain line in FIG. 7(b)). The cut 32 is formed at an angle to the surfaces of the filter 30 such that the flap portion 33 can only move into the syringe body and not towards the opening and needle, and such that when it provides a good seal to fluid moving in the opposite direction.

The filter 30 operates as follows. When the plunger is withdrawn to draw fluid up into the syringe the pressure drop causes the flap portion 33 to move on it's hinge line 34 and fluid flows through the passage which is thus provided. When the plunger is depressed to expel fluid from the syringe the flap portion 33 moves back into the position shown in FIG. 7(a) and seals. The fluid can then only pass out of the syringe by passing through the filter material itself.

For the following alternative filter embodiments features common to the foregoing filter will not be described again. All are substantially conical and comprise a ring such that they are designed to snap fit into a recess in a main body of a syringe with the apex of the cone towards the opening or needle.

Referring now to FIG. 8 a second alternative form of filter 40 is illustrated. It comprises a ring 41, a filter membrane 42 and a spring member 43 of resilient material. The spring member 43 comprises an annular portion for a snap fit onto the ring 41, and comprises a cross formation within the annular portion which define a four holes through the spring member 43. The filter membrane 42 is secured to the cross formation of the spring member 43 by adhesive or any other appropriate method. The edges of the ring 41 and filter membrane 42 are formed such that when adjacent to each other they form a seal as for the cut of the previous embodiment. This is conveniently manufactured by forming the single piece moulding as for the last embodiment and then cutting out the whole of the centre rather than making a partial cut.

The filter 40 operates as follows. When the plunger is withdrawn and fluid is drawn up into the syringe the vacuum formed pulls the spring member 43 away from the opening such that the cone is reversed, and the filter membrane 42 is pulled with it. The fluid thus flows into the syringe around the edge of the filter membrane 42 and through the holes in the spring member 43. When the plunger is depressed the pressure pushes the spring member 43 and filter membrane 42 back to the positions shown in FIG. 8(a). The filter membrane 42 seals onto the ring 41 and the fluid must pass through the filter membrane 42 if it is to be expelled from the syringe.

Referring now to FIG. 9, a third alternative form of filter 50 will be described. The filter 50 comprises a ring 51 formed in one piece with a first cross formation 52, and a second cross formation 53 which snap fits to the ring with the cross formations 52, 53 aligned. In between the two cross formations 52, 53 a filter membrane 54 is retained, with cuts 55 (shown as chain lines) in the form of arcs of circles between the cross formations 52, 53 forming four flap portions 56 with seal lines of the kind previously described. The cross formations 52, 53 are of rigid material whilst the filter membrane 54 is flexible.

The filter 50 operates as follows. When the plunger is withdrawn the drop in pressure pulls the filter membrane 54 flap portions 56 inwardly allowing the fluid to pass around the filter membrane 54. When the plunger is depressed the flap portions 56 are forced back into their positions shown in FIG. 9(a) and seal such that the fluid can only be expelled from the syringe by passing through the filter membrane 54.

Figure 10A:
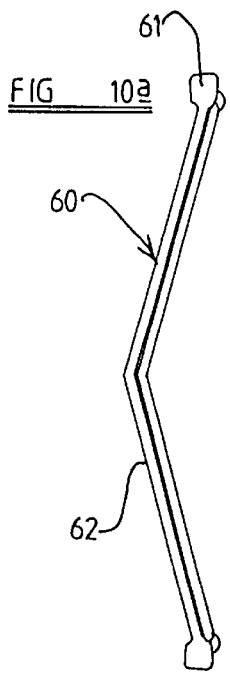
Figure 10B:
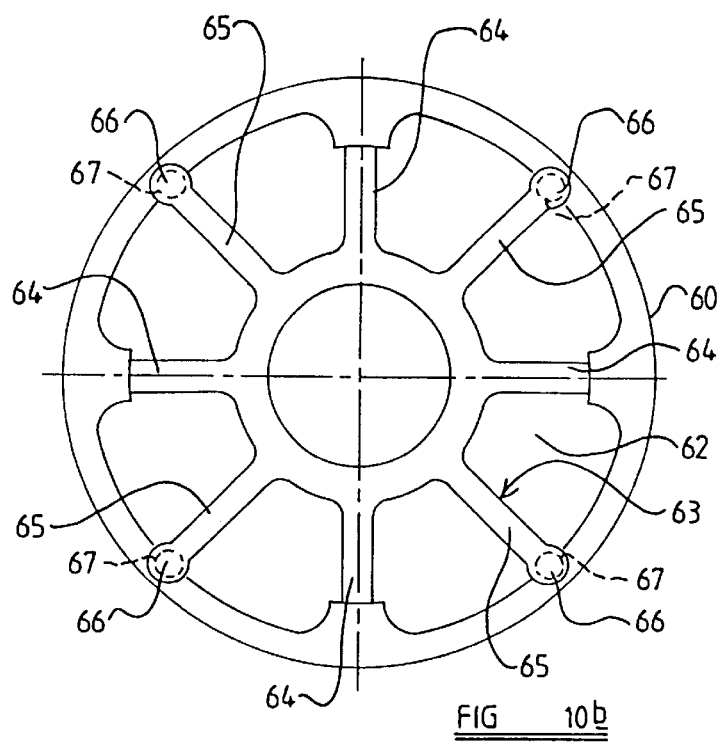

Referring now to FIG. 10 a fourth alternative filter 60 embodiment will be described. The filter 60 comprises a ring 61 and integral filter membrane 62. A spider formation 63 is formed of resilient material and comprises four legs 64 which snap fit to the ring 61, and four legs 65 with broader formations 66 at their free ends. The broader formations 66 overlie, as shown in FIG. 10(b) small holes 67 through the filter membrane 62.

The filter 60 operates as follows. When the plunger is withdrawn the pressure drop in the main body of the syringe pulls the legs 65 inwardly such that the broader formations 66 lift off the holes 67 and the fluid can pass through them. When the plunger is depressed the legs 65 are pushed back to their original position and seal the holes such that the fluid can only be expelled from the syringe by passing through the filter membrane 62.

Figure 11A:
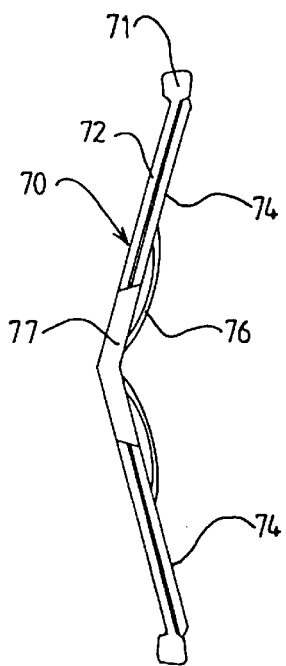
Figure 11B:
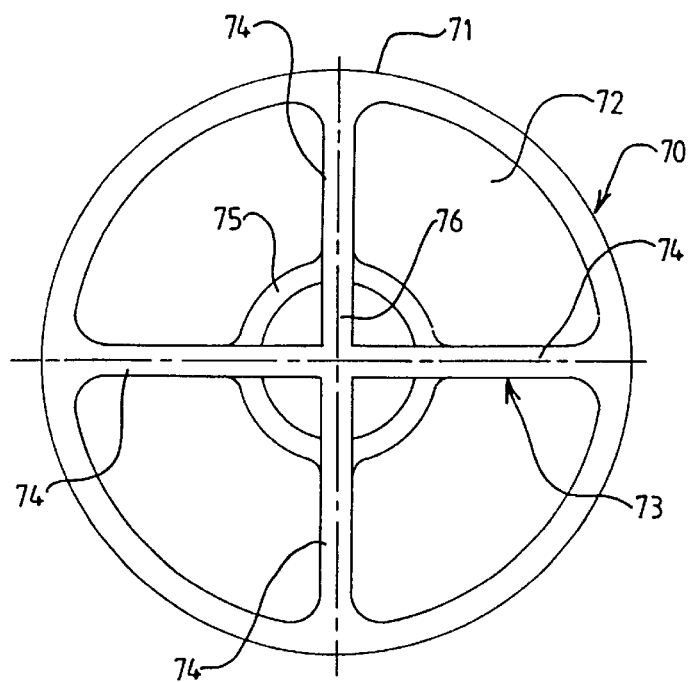

Referring now to FIG. 11 a fifth alternative filter 70 will be described. The filter 70 comprises a ring 71 formed integrally with an annular filter membrane 72. It further comprises a cross formation 73 having four legs 74 adapted to snap fit to the ring 71 and joined to a central circle 75 over which a spring member 76 is located. The spring member 76 has connected thereto a central circular valve member 77 which fits into and can seal the hole in the centre of the annular filter membrane 72.

The filter 70 operates as follows. When the plunger is withdrawn the drop in pressure pulls the spring member 76 inwardly and thus lifts the valve member 77 out of the hole in the filter membrane 72 allowing the fluid to enter. When the plunger is depressed the spring member 76 and valve member 77 are forced back to their positions shown in FIG. 11(*a*) such that the only way the fluid can leave the syringe is by passing through the filter membrane 72.

Figures 12A, 12B:
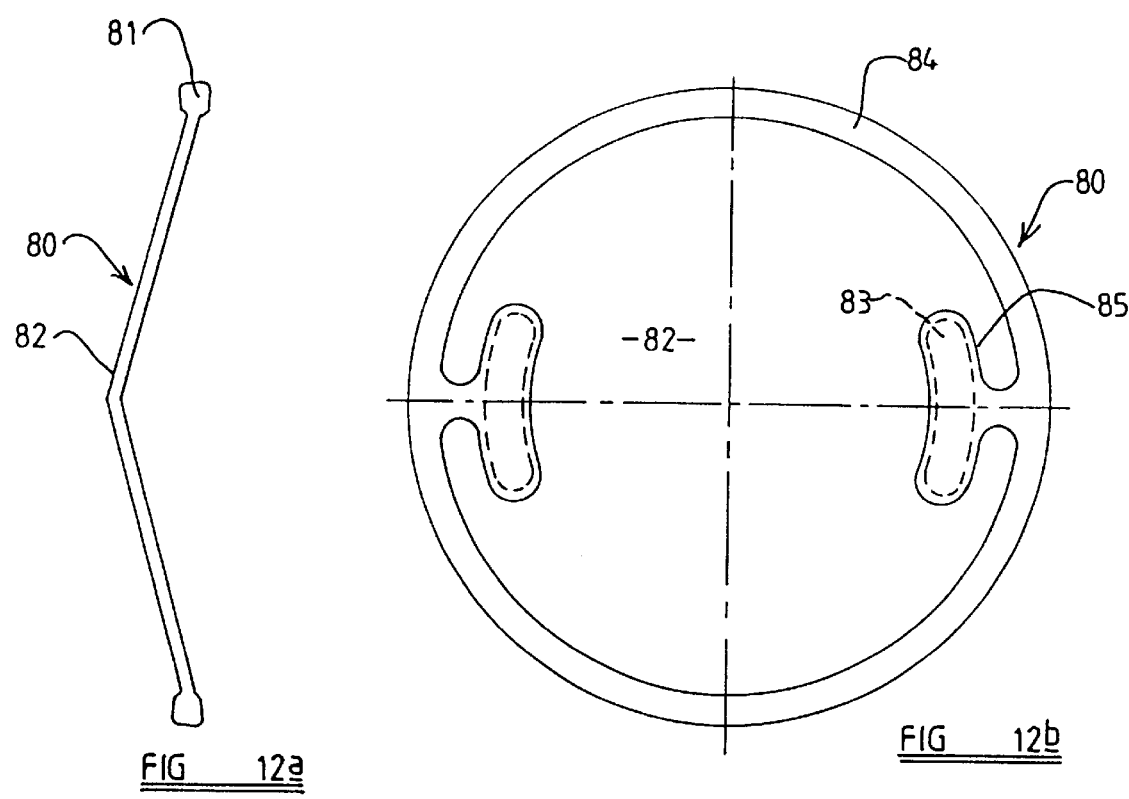

Finally, referring to FIG. 12 a sixth alternative filter 80 is will be described. The filter 80 comprises a ring 81 moulded integrally with a filter membrane 82, which provides two passages 83 there through. A second moulded component of resilient material comprises a ring 84 which snap fits to the ring 81 and carries on it two valve members 85 which overlie the passages 83 and when in the position shown in FIG. 12(*b*) seal them closed.

The filter 80 operates as follows. When the plunger is withdrawn the pressure reduction within the syringe pulls the valve members 85 inwards opening the passages 83 and the fluid flows in. When the plunger is depressed the valve members 85 are pushed back to the position where they seal the passages and the fluid can only leave the syringe by passing through the filter membrane 82.

The filter membranes in all the foregoing embodiments may be formed of any appropriate material, such as Polymide 6. The other component parts of the filters may also be formed of any appropriate materials such as those known in the prior art.

The filters described above are preferably inserted into the syringes during manufacture thereof and can thus be sterilised in-situ by known methods. However, it may be appropriate in some situations for the filters to be supplied separately for subsequent fitting.

The embodiments described above are merely examples of ways in which the invention may be implemented, many other embodiments being possible within the scope of the present invention.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A syringe comprising an opening, and a one-way filter which permits flow of fluid into the syringe, through the opening, unfiltered but which filters the fluid through a filter membrane when expelled from the syringe, the opening, wherein the filter membrane has a cut therethrough to form a permeable flap of the filter membrane portion and a hinge line, the permeable flap of the filter membrane portion moving to permit the fluid to enter the syringe unfiltered.

2. A syringe according to claim 1 wherein the filter membrane is conical, the apex of the cone pointing towards the opening.

3. A syringe according to claim 1 or 2 wherein the cut is an arc of a circle provided in the central region of the filter membrane.

4. A one-way filter which permits flow of fluid unfiltered into a syringe having an opening, but which filters the fluid when expelled from the syringe through the openings, comprising a filter membrane having a cut therethrough to form a permeable flap portion of the filter membrane and a hinge line, the flap permeable portion moving to permit the fluid to enter the syringe unfiltered.

* * * * *